(12) United States Patent
Ng et al.

(10) Patent No.: US 9,006,207 B2
(45) Date of Patent: *Apr. 14, 2015

(54) COMPOSITIONS USEFUL FOR TREATING DISORDERS RELATED TO TRPA1

(71) Applicant: Hydra BioSciences, Inc., Cambridge, MA (US)

(72) Inventors: Howard Ng, Summit, NJ (US); Jianfeng Hang, Belmont, MA (US)

(73) Assignee: Hydra Biosciences, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/736,624

(22) Filed: Jan. 8, 2013

(65) Prior Publication Data

US 2014/0005208 A1 Jan. 2, 2014

Related U.S. Application Data

(63) Continuation of application No. 12/644,108, filed on Dec. 22, 2009, now Pat. No. 8,362,025.

(60) Provisional application No. 61/139,884, filed on Dec. 22, 2008.

(51) Int. Cl.
*A61K 31/70* (2006.01)
*A61K 31/52* (2006.01)
*C07D 473/08* (2006.01)

(52) U.S. Cl.
CPC .............. *C07D 473/08* (2013.01); *A61K 31/52* (2013.01); *A61K 31/70* (2013.01)

(58) Field of Classification Search
CPC ................................. A61K 31/70; A61K 31/52
USPC ........................................ 514/45, 263, 263.23
See application file for complete search history.

(56) References Cited

U.S. PATENT DOCUMENTS

| | | | |
|---|---|---|---|
| 7,671,061 B2 * | 3/2010 | Moran et al. | 514/263.35 |
| 8,362,025 B2 * | 1/2013 | Ng et al. | 514/263.2 |
| 2009/0143377 A1 * | 6/2009 | Ng et al. | 514/234.2 |
| 2009/0163545 A1 * | 6/2009 | Goldfarb | 514/312 |
| 2011/0151018 A1 * | 6/2011 | Garrity et al. | 424/617 |
| 2012/0046305 A1 * | 2/2012 | Moran et al. | 514/263.2 |
| 2012/0108614 A1 * | 5/2012 | Chong | 514/263.23 |

FOREIGN PATENT DOCUMENTS

| | | |
|---|---|---|
| WO | 2005000309 A2 | 1/2005 |
| WO | 2007073505 A2 | 6/2007 |
| WO | 2010075353 A1 | 7/2010 |

OTHER PUBLICATIONS

International Search Report PCT/US09/69146 dated Mar. 16, 2010.

* cited by examiner

*Primary Examiner* — Raymond Henley, III
(74) *Attorney, Agent, or Firm* — Lando & Anastasi LLP

(57) ABSTRACT

Compounds and compositions for treating disorders related to TRPA1 are described herein.

10 Claims, No Drawings

COMPOSITIONS USEFUL FOR TREATING DISORDERS RELATED TO TRPA1

CLAIM OF PRIORITY

This application is a continuation of U.S. Ser. No. 12/644,108, filed Dec. 22, 2009, now U.S. Pat. No. 8,362,025, issued Jan. 29, 2013, which claims priority to U.S.S.N 61/139,884, filed Dec. 22, 2008, the entire contents of each of which is incorporated herein by reference.

BACKGROUND

The invention relates to compounds and compositions useful for treating disorders related to TRPA1.

A variety of ion channel proteins exist to mediate ion flux across cellular membranes. The proper expression and function of ion channel proteins is essential for the maintenance of cell function and intracellular communication. Numerous diseases are the result of misregulation of membrane potential or aberrant calcium handling. Given the central importance of ion channels in modulating membrane potential and ion flux in cells, identification of agents that can promote or inhibit particular ion channels are of great interest, both as research tools and as therapeutic agents.

SUMMARY OF THE INVENTION

The present invention provides compounds and compositions for treating or preventing conditions such as pain by modulating the activity of the TRPA1 channel. The compounds described herein can modulate the function of TRPA1 by inhibiting a TRPA1-mediated ion flux or by inhibiting the inward current, the outward current, or both currents mediated by TRPA1. The inhibition of a particular current can be measured by a compound's ability to inhibit or reduce such current (e.g., inward and/or outward) in an in vitro or an in vivo assay. (See Jordt et al. (2004), Nature 427:260-265; Bautista et al., (2005) PNAS: 102(34):12248-12252).

In one aspect, the invention features a compound having Formula I, shown below.

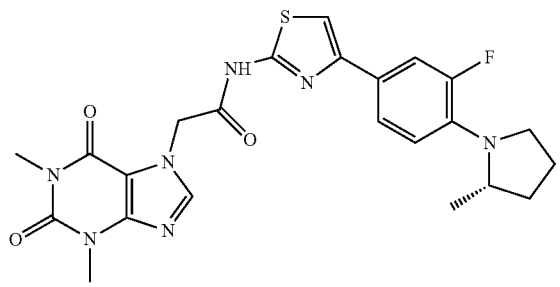 [SMILES: C[C@H]1CCCN1c1ccc(-c2csc(NC(=O)Cn3cnc4c3c(=O)n(C)c(=O)n4C)n2)cc1F]

In another aspect, the invention features a composition containing an enantiomeric excess (ee) of the compound of Formula I. For example, the composition can contain an ee of at least 50%, 75%, 90%, 95%, or 99%. The invention also features salts of the compound made from mineral acids, such as hydrochloric acid, hydrobromic acid, sulfuric acid and phosphoric acid. In one embodiment, the invention features the hydrochloride salt of the compound of Formula I. In one embodiment, the invention features a composition comprising the hydrochloride salt of the compound of Formula I. For example, the composition can contain an ee of at least 50%, 75%, 90%, 95%, or 99%.

Any of the compounds disclosed herein may be used to treat any diseases disclosed herein. In addition, these compounds may be used to inhibit a function of a TRPA1 channel in vitro or in vivo.

DETAILED DESCRIPTION OF THE INVENTION

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

Some of the compositions described herein contain an enantiomeric excess of at least 50%, 75%, 90%, 95%, or 99% of Compound 1 (the S-enantiomer). In other words the compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as for example tritium ($^3H$) or carbon-14 ($^{14}C$). All isotopic variations of the compounds disclosed herein, whether radioactive or not, are intended to be encompassed within the scope of the present invention. For example, deuterated compounds or compounds containing $^{13}C$ are intended to be encompassed within the scope of the invention.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", J. Pharm. Sci. 66:1-19.)

Certain compounds disclosed herein can exist in unsolvated forms as well as solvated forms, including hydrated forms. In general, the solvated forms are equivalent to unsolvated forms and are encompassed within the scope of the present invention. Certain compounds disclosed herein may exist in multiple crystalline or amorphous forms. In general, all physical forms are equivalent for the uses contemplated by the present invention and are intended to be within the scope of the present invention.

An "effective amount" of, e.g., a TRPA1 antagonist, with respect to the subject methods of inhibition or treatment, refers to an amount of the antagonist in a preparation which, when applied as part of a desired dosage regimen brings about a desired clinical or functional result. Without being bound by theory, an effective amount of a TRPA1 antagonist for use in the methods of the present invention, includes an amount of a TRPA1 antagonist effective to decrease one or more in vitro or in vivo functions of a TRPA1 channel. Exemplary functions include, but are not limited to, membrane polarization (e.g., an antagonist may promote hyperpolarization of a cell), ion flux, ion concentration in a cell, outward current, and inward current. Compounds that antagonize TRPA1 function include compounds that antagonize an in vitro or in vivo functional activity of TRPA1. When a particular functional activity is only readily observable in an in vitro assay, the ability of a compound to inhibit TRPA1 function in that in vitro assay serves as a reasonable proxy for the activity of that compound. In certain embodiments, an effective amount is an amount sufficient to inhibit a TRPA1-mediated current and/or the amount sufficient to inhibit TRPA1 mediated ion flux.

The term "hydrate" as used herein, refers to a compound formed by the union of water with the parent compound.

The term "oxidative metabolite" is intended to encompass compounds that are produced by metabolism of the parent compound under normal physiological conditions. Specifically, an oxidative metabolite is formed by oxidation of the parent compound during metabolism. For example, a thioether group may be oxidized to the corresponding sulfoxide or sulfone.

The term "solvate" as used herein, refers to a compound formed by solvation (e.g., a compound formed by the combination of solvent molecules with molecules or ions of the solute).

The terms "TRPA1," "TRPA1 protein," and "TRPA1 channel" are used interchangeably throughout the application. These terms refer to an ion channel (e.g., a polypeptide) comprising the amino acid sequence set forth in SEQ ID NO: 1, SEQ ID NO:3, or SEQ ID NO: 5 of WO 2007/073505, or an equivalent polypeptide, or a functional bioactive fragment thereof.

The term "treating" includes prophylactic and/or therapeutic treatments. The term "prophylactic or therapeutic" treatment refers to administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

Indications

Modulating the function of TRPA1 proteins provides a means of modulating calcium homeostasis, sodium homeostasis, membrane polarization, and/or intracellular calcium levels, and compounds that can modulate TRPA1 function are useful in many aspects, including, but not limited to, maintaining calcium homeostasis, modulating intracellular calcium levels, modulating membrane polarization, and treating or preventing diseases, disorders, or conditions associated with calcium and/or sodium homeostasis or dyshomeostasis.

Thus, TRPA1 antagonists can be used as part of a prophylaxis or treatment for a variety of disorders and conditions, described in more detail below. In other embodiments, the invention provides methods and compositions for inhibiting a function of a TRPA1 channel in vitro or in vivo. The compounds and compositions described herein can be used in the treatment of any of the foregoing or following diseases or conditions, including in the treatment of pain associated with any of the foregoing or following diseases or conditions.

In certain embodiments, the compounds and compositions disclosed herein can be used to treat or ameliorate pain. Exemplary classes of pain that can be treated include, but are not limited to nociceptive pain, inflammatory pain, and neuropathic pain. The pain can be chronic or acute.

TRPA1 inhibitors may be particularly useful in the treatment of pain associated with cancer, osteoarthritis, rheumatoid arthritis, post-herpetic neuralgia, burns, and other indications detailed above and below.

The compounds and compositions disclosed herein may also be used in connection with prevention or treatment of sensitivity to pain and touch. Pain or sensitivity to pain and touch may be indicated in a variety of diseases, disorders or conditions, including, but not limited to, diabetic neuropathy, breast pain, psoriasis, eczema, dermatitis, burn, post-herpetic neuralgia (shingles), peripheral neuropathic and central neuropathic pain, cancer and tumor pain, spinal cord injury, crush injury and trauma induced pain, migraine, cerebrovascular and vascular pain, sickle cell disease pain, rheumatoid arthritis pain, musculoskeletal pain including treating signs and symptoms of osteoarthritis and rheumatoid arthritis, orofacial and facial pain, including dental pain, temperomandibular disorder, and cancer related, lower back or pelvic pain, surgical incision related pain, inflammatory and non-inflammatory pain, visceral pain, psychogenic pain and soft tissue inflammatory pain, reflex sympathetic dystrophy, and pain resulting from kidney stones or urinary tract infection.

The compounds and compositions described herein may also be used to treat oral pain. The term "oral pain" refers to any pain in the mouth, throat, lips, gums, teeth, tongue, or jaw. The term is used regardless of the cause of the pain and regardless of whether the oral pain is a primary or secondary symptom of a particular disease, injury, or condition.

The oral pain can be caused by ulcers, sores, or other lesions in the mouth. For example, oral pain may be caused by ulcers, sores, or other lesions on the tongue, gums, lips, throat, or other tissues of the mouth. Alternatively or additionally, oral pain may be caused by inflammation of the throat, tongue, gums, lips, or other tissues of the mouth. Inflammation may accompany ulcers or other lesions, or inflammation may occur prior to or in the absence of formation of ulcers or other lesions.

The compounds and compositions disclosed herein can also be useful to treat fibromyalgia (FMS; fibromyalgia syndrome); Complex Regional Pain Syndrome (CRPS; also known as chronic regional pain syndrome); respiratory conditions such as obstructive diseases such as chronic obstructive pulmonary disease (COPD), emphysema, chronic bronchitis, asthma (including asthma caused by industrial irritants), cystic fibrosis, bronchiectasis, bronchiolitis, allergic bronchopulmonary aspergillosis, and tuberculosis; restrictive lung disease including asbestosis, radiation fibrosis, hypersensitivity pneumonitis, infant respiratory distress syndrome, idiopathic pulmonary fibrosis, idiopathic pulmonary fibrosis, idiopathic interstial pneumonia sarcoidosis, eosinophilic pneumonia, lymphangioleiomyomatosis, pulmonary Langerhan's cell histiocytosis, and pulmonary alveolar proteinosis; respiratory tract infections including upper respiratory tract infections (e.g., common cold, sinusitis, tonsillitis, pharyngitis and laryngitis) and lower respiratory tract infections (e.g., pneumonia); respiratory tumors whether malignant (e.g., small cell lung cancer, non-small cell lung cancer, adenocarcinoma, squamous cell carcinoma, large cell undifferentiated carcinoma, carcinoid, mesothelioma, metastatic cancer of the lung, metastatic germ cell cancer, metastatic renal cell carcinoma) or benign (e.g., pulmonary hamartoma, congenital malformations such as pulmonary sequestration and congenital cystic adenomatoid malformation (CCAM)); pleural cavity diseases (e.g., empyema and mesothelioma); and pulmonary vascular diseases (e.g, pulmonary embolism such as thromboembolism, and air embolism (iatrogenic), pulmonary arterial hypertension, pulmonary edema, pulmonary hemorrhage, inflammation and damage to capillaries in the lung resulting in blood leaking into the alveoli. Other conditions that may be treated include disorders that affect breathing mechanics (e.g., obstructive sleep apnea, central sleep apnea, amyotrophic lateral sclerosis, Guillan-Barre syndrome, and myasthenia gravis). The present compounds can also be useful for treating, reducing, or preventing one or more symptoms associated with respiratory conditions including, for example, shortness of breath or dyspnea, cough (with or without the production of sputum), coughing blood (haemoptysis), chest pain including pleuritic chest pain, noisy breathing, wheezing, and cyanosis.

The compounds and compositions can be used to treat skin diseases or disorders that are characterized by epidermal hyperplasia, a condition in which skin cells both proliferate too rapidly and differentiate poorly. Such diseases include psoriasis, and basal and squamous cell carcinomas. Many dermatological disorders are accompanied by itch (pruritus). Pruritus and pain share many mechanistic similarities. Both are associated with activation of C-fibers, both are potentiated by increases in temperature and inflammatory mediators and both can be quelled with opiates. Decreasing neuronal excitability, particularly C-fiber excitability may alleviate pruritus associated with dialysis, dermatitis, pregnancy, poison ivy, allergy, dry skin, chemotherapy and eczema.

The compounds and compositions can be used to treat neurodegenerative diseases and disorders such as Alzheimer's disease (AD), Parkinson's disease, Huntington's disease, amyotrophic lateral sclerosis (ALS), and other brain disorders caused by trauma or other insults including aging.

The compounds and compositions provided herein may also be used in connection with treatment of inflammatory diseases. These diseases include but are not limited to asthma, chronic obstructive pulmonary disease, rheumatoid arthritis, osteoarthritis, inflammatory bowel disease, glomerulonephritis, neuroinflammatory diseases such as multiple sclerosis, and disorders of the immune system.

The compounds and compositions can be used to treat neuropathy, for example diabetic neuropathy or other peripheral neuropathies. In addition to their use in the treatment of peripheral neuropathies (e.g., reducing inflammation), the subject inhibitors may also be useful in reducing the pain associated with peripheral neuropathy. They can also be used to treat pancreatitis, either acute pancreatitis or chronic pancreatitis.

The compounds and compositions provided herein may also be used in connection with treatment of malignancies, including, but not limited to, malignancies of lymphoreticular origin, bladder cancer, breast cancer, colon cancer, endometrial cancer, head and neck cancer, lung cancer, melanoma, ovarian cancer, prostate cancer and rectal cancer, in addition to skin cancers described above.

In addition, pain associated with cancer or with cancer treatment is a significant cause of chronic pain. Cancers of the bone, for example, osteosarcoma, are considered exceptionally painful, and patients with advanced bone cancer may require sedation to tolerate the intense and persistent pain. Accordingly, TRPA1 antagonists of the invention represent a significant possible therapeutic for the treatment of pain, for example, the pain associated with cancer or with cancer treatment.

The compounds and compositions can be used to treat incontinence; to modulate the sensation of cool, cold and decreased temperatures that often accompany pain; to treat hypertension; oral mucositis (also known as stomatitis); canker sores, also known as aphthous ulcers (aphthae); gastroesophageal reflux disease, or GERD; gingivostomatitis; oral thrush; glossitis; cutaneous diseases such as lichen planus, pemphigus, pemphigoid, and erythema multiforme; Crohn's disease, ulcerative colitis, irritable bowel syndrome, celiac sprue, and dermatitis herpetiformis.

The compounds and compositions disclosed herein may be used to help manage the pain and discomfort of oral inflammation, lesions, or ulcers caused by any of these gastrointestinal conditions. In addition, the compounds can be used to treat psoriasis and basal cell and squamous cell caricinomas, a neurodegenerative disease or disorder, e.g., Alzheimer's disease (AD), Parkinson's disease, Huntington's disease, amyotrophic lateral sclerosis (ALS), and other brain disorders caused by trauma or other insults including aging, inflammatory bowel disease, glomerulonephritis, neuroinflammatory diseases, multiple sclerosis, and disorders of the immune system), cancer (e.g. liposarcoma) or other proliferative disease, kidney disease and liver disease, a metabolic disorder such as diabetes. Additional conditions include metabolic diseases and disorders including obesity and diabetes; liver and kidney diseases and disorders; aging-related disorders; ATP-related diseases or disorders including epilepsy, cognition, emesis, asthma, peripheral vascular disease, irritable bowel syndrome, cystitis, depression, aging-associated degenerative diseases, cystic fibrosis, diabetes, rheumatoid diseases, Sjogren's Syndrome, allergies, allergic rhinitis, Fabry's disease, and injuries from chemical warfare agents including, for example, nerve agents, blood agents, blister agents, pulmonary agents, incapacitating agents, and toxins.

Combination Therapy

The subject compounds can be used alone or in combination with other pharmaceutically active agents. Examples of such other pharmaceutically active agents include, but are not limited to, anti-inflammatory agents (e.g., NSAIDS, bradykinin receptor antagonists, hormones and autacoids such as corticosteroids), anti-acne agents (e.g., retinoids), anti-wrinkle agents, anti-scarring agents, anti-incontinence agents (such as M1-receptor antagonists) anti-emetics (such as NK1 antagonists), anti-psoriatic agents, antacids, anti-proliferative agents (e.g., anti-eczema agents, anti-cancer), anti-fungal agents, anti-viral agents, anti-septic agents (e.g., antibacterials), local anaesthetics, anti-migraine agents, keratolytic agents, and other agents used for the treatment of skin diseases or conditions.

In certain embodiments, a compound of the invention is conjointly administered with an analgesic. Suitable analgesics include, but are not limited to, opioids, glucocorticosteroids, non-steroidal anti-inflammatories, naphthylalkanones, oxicams, para-aminophenol derivatives, propionic acids, propionic acid derivatives, salicylates, fenamates, fenamate derivatives, pyrozoles, and pyrozole derivatives. Examples of such analgesic compounds include, but are not limited to, codeine, hydrocodone, hydromorphone, levorpharnol, morphine, oxycodone, oxymorphone, butorphanol, dezocine, nalbuphine, pentazocine, etodolac, indomethacin, sulindac, tolmetin, nabumetone, piroxicam, acetaminophen, fenoprofen, flurbiprofen, ibuprofen, ketoprofen, naproxen, diclofenac, oxaprozin, aspirin, diflunisal, meclofenamic acid, mefanamic acid, prednisolone, and dexamethasone. Preferred analgesics are non-steroidal anti-inflammatories and opioids (preferably morphine).

In some embodiments, the compounds disclosed herein can be administered in conjunction with a therapeutic whose administration causes pain. For example, a TRPA1 antagonist can be administered in conjunction with an anesthetic, to reduce the pain caused by the administration of the anaesthetic. A TRPA1 antagonist can also be administered in conjunction with a chemotherapeutic agent, to reduce the pain caused by administration of the chemotherapeutic agent.

In certain embodiments, a compound of the invention is conjointly administered with a non-steroidal anti-inflammatory. Suitable non-steroidal anti-inflammatory compounds include, but are not limited to, piroxicam, diclofenac, etodolac, indomethacin, ketoralac, oxaprozin, tolmetin, naproxen, flubiprofen, fenoprofen, ketoprofen, ibuprofen, mefenamic acid, sulindac, apazone, phenylbutazone, aspirin, celecoxib and rofecoxib.

In addition to TRPA1, other TRP channels have been implicated in pain reception and/or sensation. For example, certain TRPM channels including TRPM8 have been implicated in the reception and/or sensation of pain. Accordingly, in certain embodiments, the methods of the present invention include treating pain by administering (i) a combination of a selective TRPA1 antagonist and a selective TRPM8 antagonist; (ii) a combination of a selective TRPA1 antagonist, a selective TRPM8 antagonist, and one or more of a selective TRPV1 and/or TRPV3 antagonist; (iii) a cross-TRP inhibitor that antagonizes a function of TRPA1 and TRPM8; or (iv) a pan inhibitor that antagonizes a function of TRPA1, TRPM8, and one or more of TRPV1 and TRPV3.

Pharmaceutical Compositions

While it is possible for a compound disclosed herein to be administered alone, it is preferable to administer the compound as a pharmaceutical formulation, where the compound is combined with one or more pharmaceutically acceptable excipients or carriers. The compounds disclosed herein may be formulated for administration in any convenient way for use in human or veterinary medicine. In certain embodiments, the compound included in the pharmaceutical preparation may be active itself, or may be a prodrug, e.g., capable of being converted to an active compound in a physiological setting.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Examples of pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; (21) cyclodextrins such as Captisol®; and (22) other non-toxic compatible substances employed in pharmaceutical formulations.

Examples of pharmaceutically acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Solid dosage forms (e.g., capsules, tablets, pills, dragees, powders, granules and the like) can include one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents.

Liquid dosage forms can include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Ointments, pastes, creams and gels may contain, in addition to an active compound, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to an active compound, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient that can be combined with a carrier material to produce a single dosage form will generally be that amount of the compound which produces a therapeutic effect.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants that may be required.

When the compounds disclosed herein are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The formulations can be administered topically, orally, transdermally, rectally, vaginally, parentally, intranasally, intrapulmonary, intraocularly, intravenously, intramuscularly, intraarterially, intrathecally, intracapsularly, intraorbitally, intracardiacly, intradermally, intraperitoneally, transtracheally, subcutaneously, subcuticularly, intraarticularly, subcapsularly, subarachnoidly, intraspinally, intrasternally or by inhalation.

Dosages

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound disclosed herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound that is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms. In some embodiments, the dose will be 1-20, or 5-10 mg per kilogram of body weight, administered twice daily.

EXAMPLES

The following examples are intended to be illustrative, and are not meant in any way to be limiting.

Example 1

Synthesis of Compound 1

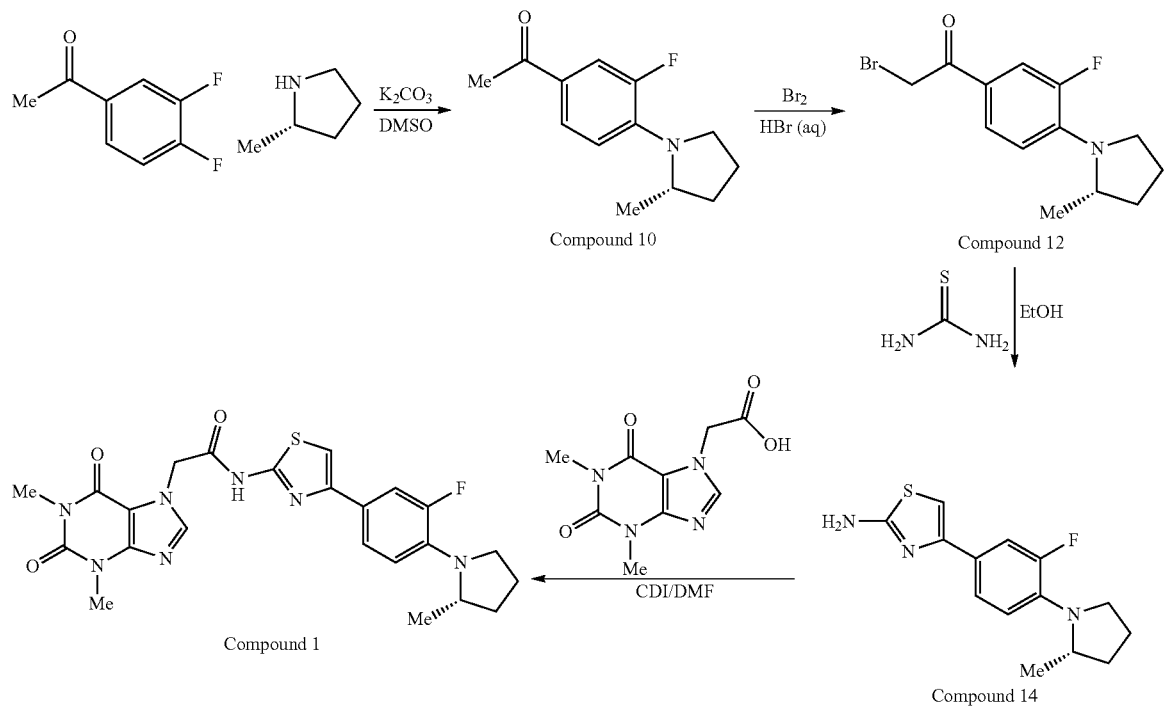

Step 1: Synthesis of Compound 10 (3'-F,4'-[(S)-2-methylpyrrolidino]acetophenone)

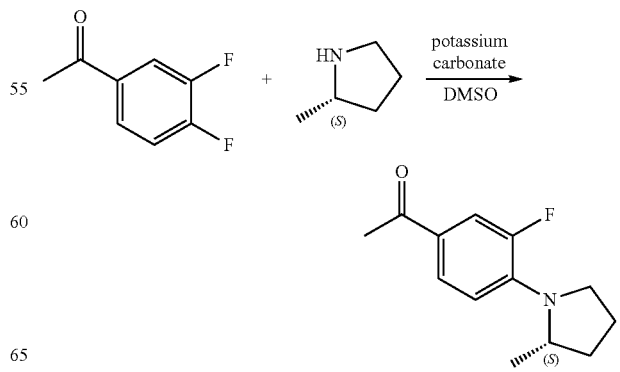

A 100 mL 3-necked round-bottomed flask was equipped with an overhead mechanical stirrer, nitrogen inlet and reflux condenser. To potassium carbonate, powdered (6.49 g, 47.0 mmol) in the flask was added DMSO (40 mL). The solid was gently stirred while (S)-2-methylpyrrolidine, >99% ee, (4.80 ml, 47.0 mmol) and 3,4-difluoroacetophenone (5.35 ml, 42.7 mmol) were added. The solid remained free-flowing while the liquid portion turned light yellow. The mixture was heated to 60° C. with an oil bath. After 1 hour, the oil bath temperature was increased to 80° C. LCMS analysis of the reaction mixture after 5 hours indicated the reaction was complete. The reaction mixture was cooled, and poured into a 250 mL separatory funnel containing 60 mL ethyl ether and 60 mL water. The reaction vessel was rinsed with 30 mL of water and 30 mL of ethyl ether and the washings were added to the separatory funnel. After shaking, the layers were separated, and the aqueous layer was back-extracted with an additional 60 mL of ethyl ether. The combined organic layers were washed with 30 mL water, 60 mL 0.1 M $H_3PO_4$ (which removed some color), 30 mL saturated sodium bicarbonate, 30 mL brine. The solution was dried over sodium sulfate, and concentrated via rotary evaporation to an amber oil, ~9.5 g. The solution was passed through a plug of silica gel (60 g), packed into a large fritted filter funnel, topped with sand. The yellow solution was concentrated via rotary evaporation to give a yellow oil, 9.307 g, 98% yield. Mass spectrum: 222 $(M+1)^+$.

Step 2: Preparation of Compound 12

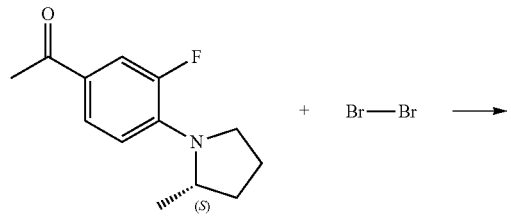

To the product from Step 1 (34.0 g, 154 mmol) in 102 mL of isopropyl acetate was added 168 mL of HBr (47%). The addition was exothermic. Bromine (24.55 g, 154 mmol) was added to this mixture at 18-24° C. The mixture was stirred for 4 hours. Analysis by LCMS showed 11.8% starting ketone, 81.7% desired mono-brominated product, and 6.4% di-brominated product. The reaction mixture was added to a mixture of 480 mL water and 340 mL dichloromethane at 5-10° C. The mixture was stirred and warmed to 18-24° C. The phases were separated and the organic phase was washed with 100 mL of saturated sodium bicarbonate solution. Subsequently the organic phase was washed twice with 50 mL of water each time. The solution was concentrated under vacuum to yield Compound 12 as an oil (42.8 g, 92.3%). Mass spectrum: 300, 302 $(M+1)^+$.

Step 3: Preparation of 4-(3-F,4-(S)-2-methylpyrrolidinophenyl)aminothiazole hydrobromide

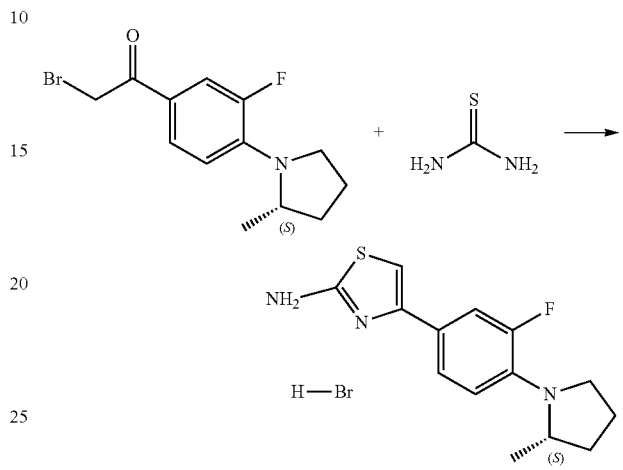

The product of Step 2 (21.1 g, 70 mmol) was dissolved in 106 mL dichloromethane and added to a suspension of thiourea (4.28 g, 56 mmol) in 53 mL of ethanol at 0-5° C. After 1 hr the conversion was complete as determined by LCMS and 295 mL of isopropyl acetate was added over 30 min at 0-5° C. The formed suspension was stirred for 2 hrs at 0-5° C. The product was filtered and washed with 40 mL isopropyl acetate. After drying under vacuum at 50° C., 18.0 g, 71.4% of the product was isolated as a off white solid. (Purity 99.44 area %). Mass spectrum: 278 $(M+1)^+$.

Step 4

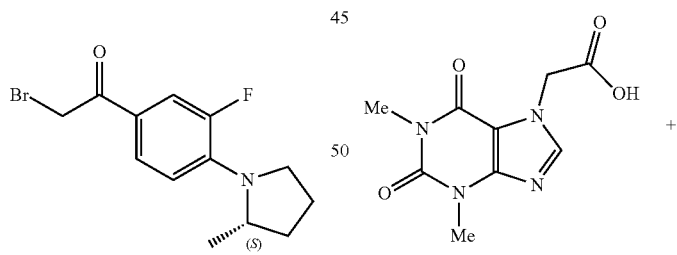

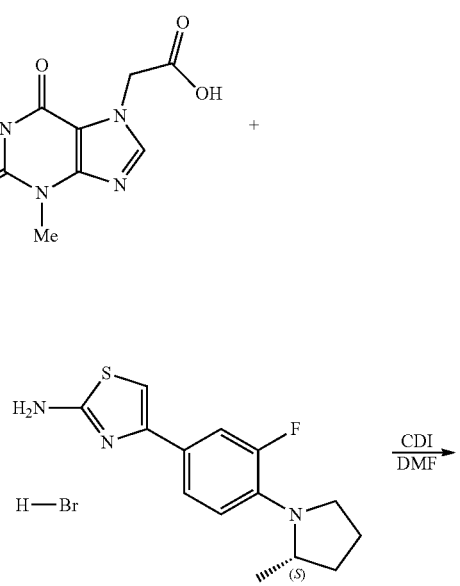

-continued

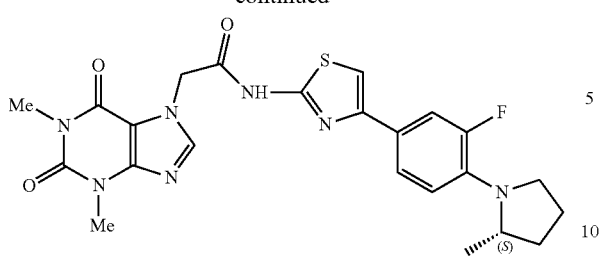

Theophylline-7-acetic acid (17.55 g, 74 mmol) and 0.82 g of 4-dimethylaminopyridine were suspended in 72 mL of DMF. A solution of 16.29 g, 100 mmol) 1,1'-carbonyldiimidazole in 96 mL of DMF was added at 18-24° C. and rinsed with 5 mL of DMF. During stirring for 30 min. a clear solution was formed, which was heated to 50° C. At this temperature a solution of the product of Step 3 (24 g, 67 mmol) in 120 mL of DMF was added. The line was rinsed with 5 mL of DMF. The mixture was heated for 6.5 hrs at 50° C. and subsequently at room temperature for two days. The product suspension was heated to 50° C. and 180 mL of water was added. The suspension was cooled to 18-24° C. over about 2 hours and filtered. The product was washed with 240 mL of water in portions. Wet product (81.0 g) was isolated. The wet crude product (64 g) was suspended in 285 mL of ethanol and heated to reflux for 30 min. The suspension was cooled to room temperature. The product was filtered and washed with 80 mL of ethanol. After drying, 22.0 g (83% yield) of Compound 1 was isolated. Mass spectrum: 498 (M+1)$^+$.

Example 2

Formation of the HCl Salt

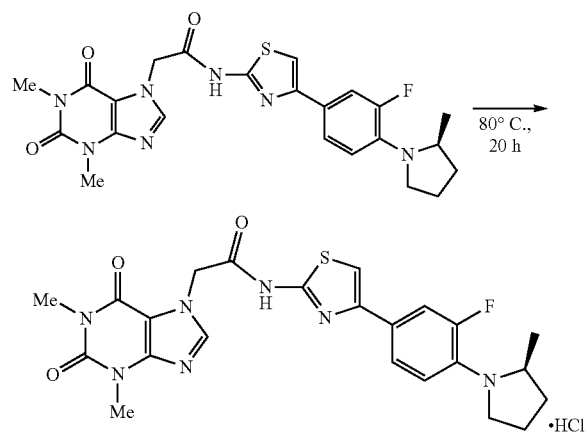

Compound 1 (200 mg, 0.402 mmol) was suspended and stirred in aq. HCl solution (1.0 N, 5.0 mL) at 80° C. for 20 h under the atmosphere of argon. The mixture was cooled to room temperature, then filtered. The solid was washed with ethanol (10 mL), then ether (20 mL). The resulting white solid was dried in vacuo to give 192 mg of the corresponding HCl salt in 89% yield. m.p. 249° C.

Example 3

Inhibition of TRPA1

Compound 1 was tested using a procedure similar to the procedure outlined in WO 2007/073505. The $IC_{50}$ of Compound 1 against hTRPA1 channel activity was found to be about 4 nM.

Example 4

Effect of Compound 1 on Formalin-Induced Pain Behavior in Rats

Compound 1 was tested in the formalin-induced pain test reported by Dubuisson et al., *Pain* 1977 December; 4(2):161-74. The compound was dosed orally in rats (8 animals) at 50 mg/kg, one hour prior to intraplantar formalin (3%) injection. The control group (8 animals) received vehicle (30% Captisol® in water, pH 10). The duration of pain behaviors was observed for 2 minutes following the injection. The duration of pain behavior in the treated animals was reduced by about 30%, compared to the animals who received vehicle.

Example 5

Effect of Compound 1 on AITC-Induced Pain Behavior in the Rat

Compound 1 was tested in the automated flinch detecting system described by Yaksh et al., J. Appl. Physiol 90: 2386-2402 (2001). A small metal band was loosely placed around each rat's left hind paw. The fasted rats were dosed (50 mg/kg) via oral gavage with Compound 1 (8 animals) or vehicle (8 animals, 30% Captisol® in water, pH 10). The rats were acclimatized in the test chamber prior to allyl isothiocyanate (AITC) administration. AITC was then injected into the paw of each animal, and the animal was promptly returned to the chamber. The number of paw flinches was monitored for 60 minutes. After 10 minutes, animals receiving vehicle flinched a total of about 350 times, while the treated animals flinched about 200 times. After 60 minutes the animals that had received vehicle prior to AITC administration flinched about 1950 times, while the compound pre-treated animals flinched about 1000 times. These results demonstrate that Compound 1 was able to reduce the AITC-induced pain behavior in rats.

INCORPORATION BY REFERENCE

All publications and patents mentioned herein are hereby incorporated by reference in their entirety as if each individual publication or patent was specifically and individually indicated to be incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

We claim:
1. A method for treating chronic or acute pain in a human, the method comprising administering an effective amount of a composition comprising a compound of Formula I, or a pharmaceutically acceptable salt thereof

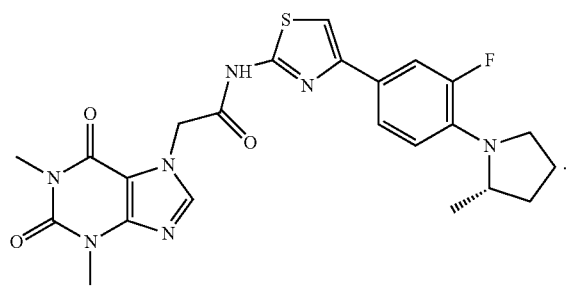

Formula I

2. The method of claim 1, wherein the composition contains an enantiomeric excess of at least 50% of a compound of Formula I.

3. The method of claim 1, wherein the composition contains an enantiomeric excess of at least 75% of a compound of Formula I.

4. The method of claim 1, wherein the composition contains an enantiomeric excess of at least 90% of a compound of Formula I.

5. The method of claim 1, wherein the composition contains an enantiomeric excess of at least 95% of a compound of Formula I.

6. The method of claim 1, wherein the composition contains an enantiomeric excess of at least 99% of a compound of Formula I.

7. The method of claim 1, wherein the composition contains a pharmaceutically acceptable salt of the compound of Formula I.

8. The method of claim 7, wherein the pharmaceutically acceptable salt is a hydrochloride, hydrobromide, sulfate, or phosphate salt of a compound of Formula I.

9. The method of claim 1, comprising treating the human for chronic pain.

10. The method of claim 1, comprising treating the human for acute pain.

* * * * *